United States Patent [19]

Wada et al.

[11] Patent Number: 4,990,698

[45] Date of Patent: Feb. 5, 1991

[54] METHOD FOR PRODUCING ALKADIENOLS

[75] Inventors: Keisuke Wada, Yokohama; Keiichi Sato, Tokyo; Yukio Kasori, Yokkaichi; Yoko Misu, Tokyo, all of Japan

[73] Assignee: Mitsubishi Kasei Corporation, Tokyo, Japan

[21] Appl. No.: 404,574

[22] Filed: Sep. 8, 1989

[30] Foreign Application Priority Data

Sep. 26, 1988 [JP] Japan ................................ 63-240269
Jun. 14, 1989 [JP] Japan ................................ 1-151337

[51] Int. Cl.$^5$ ...................... C07C 29/36; C07C 29/46; C07C 33/02; C07C 31/36
[52] U.S. Cl. ................................. 568/909.5; 568/845
[58] Field of Search ............................ 568/909.5, 845

[56] References Cited

U.S. PATENT DOCUMENTS 3,670,032  6/1972  Romanelli ..................... 568/909.5
4,417,079 11/1983  Yoshimura et al. ............ 568/909.5

FOREIGN PATENT DOCUMENTS 1354507  9/1971  United Kingdom ............ 568/909.5

Primary Examiner—J. E. Evans
Attorney, Agent, or Firm—Oblon, Spivak, McClelland, Maier & Neustadt

[57] ABSTRACT

An improving method for producing alkadienols by reaction of conjugated alkadiene and water in the presence of carbon dioxide and a catalyst composed of a palladium compound and phosphine (or phosphite), wherein the by-products having high boiling point and the palladium catalyst are efficiently separated from the reaction product for re-use without impairing their effectiveness as the catalyst.

23 Claims, No Drawings

METHOD FOR PRODUCING ALKADIENOLS

The present invention relates to a method for producing alkadienols, and, more particularly, it is concerned with a method for producing alkadienols which are hydrated dimers of a conjugated alkadiene, by the reaction between conjugated alkadiene and water in the presence of carbon dioxide and a catalyst composed of a palladium compound and phosphine (or phosphite).

Of various alkadienols, octadienol is a particularly important compound, in the chemical industry, as an intermediate for producing n-octanol and its ester, or else.

As the method for production of alkadienols, there has heretofore been proposed a method, by which a conjugated alkadiene and water are reacted in the presence of carbon dioxide and a catalyst composed of a palladium compound and phosphine or phosphite (vide: Japanese Examined Patent Publication No. 10565/1975). When the reaction for producing alkadienols is carried out in a liquid phase according to this method, both conjugated alkadiene and water are simultaneously brought into contact with the above-mentioned catalytic component, and the thus produced alkadienols are separated from the catalyst by means of distillation, or other expedients. This operation is done either in a continuous process or in a batch-wise process. Thereafter, the liquid catalyst containing at least the palladium compound and phosphine (or phosphite) is again circulated into the reaction system for further use.

The applicant of the present invention, on the other hand, previously proposed a method for effectively circulating the catalyst for its re-use, at the time of producing alkadienols, wherein at least a part of the liquid reaction product is brought into contact with a basic substance to separate by extracting high boiling point by-products contained in the liquid reaction product, after which liquid extraction residue containing therein the catalyst is supplied for the above-mentioned reaction (vide: Japanese Examined Patent Publication No. 6807/1986).

However, in the reaction for producing alkadienols from conjugated alkadiene and water as disclosed in the Japanese Examined Patent Publication No. 10565/1975 referred to above, there is unavoidably produced high boiling point substances due to side-reaction, which substances will gradually accumulate in the liquid catalyst to be circulated for further use. Such high boiling point substances to be accumulated in the liquid catalyst is not only diluted substances of no use per se, but also exhibits chemical suppressing action against the catalyst activity, or considerably hinders progress in the reaction by unnecessarily increasing viscosity of the liquid catalyst.

Since the liquid catalyst containing therein expensive materials such as palladium, phosphine, phosphite, and others, there will be a great economical loss, if these catalytic components are not used effectively. Therefore, the separation and removal of the accumulated high boiling point substances from the liquid catalyst by an economical expedient, without spoiling the catalytic activity, have been one of the most important problems for the industrially effective production of alkadienols.

By the way, a method as disclosed in the Japanese Examined Patent Publication No. 6807/1986 is to separate by extracting high boiling point by-products contained in the liquid reaction product, and to circulate the liquid extraction residue containing therein the palladium catalyst in the reaction system without depositing the palladium complex, hence the activity of the catalyst to be circulated becomes apprehensively lowered to some extent.

The present invention aims at solving these various problems inherent in the conventional methods, and providing an improved method for producing alkadienols from the reaction between conjugated alkadiene and water in the presence of carbon dioxide and a catalyst composed of a palladium compound, phosphine (or phosphite], wherein the by-products having high boiling point is efficiently separated from the palladium catalyst for reuse without impairing its effectiveness as the catalyst.

In view of the above-mentioned circumstances which have been predominant in the conventional technique, the present inventors conducted strenuous reseaches and studies through various experiments on the method of separating the high boiling point by-products from the palladium catalyst in the reaction for producing alkadienols from conjugated alkadiene and water in the presence of carbon dioxide and a catalyst composed of a palladium compound and phosphine (or phosphite). As the result of this, they have found out that, by depositing the palladium complex from solution containing at least the high boiling point by-products and the palladium catalyst, such high boiling point by-products can be efficiently separated from the palladium catalyst without impairing its effectiveness as the catalyst. On the basis of this finding, they have completed the present invention.

According to the present invention, in its broadest definition, there is provided a method for producing alkadienols by reaction of conjugated alkadiene and water in the presence of carbon dioxide and a catalyst composed of a palladium compound and phosphine (or phosphite), characterized in that a palladium complex is deposited from at least a part of the liquid reaction product to be obtained by said reaction, after which the palladium complex is again fed into said reaction system.

In the following, the present invention will be described in detail with respect to the materials used and the reaction conditions to be adopted for the practice of the method.

The conjugated alkadiene which is capable of producing alkadienols by its reaction with water in accordance with the method of the present invention may be selected from the following: 1,3-butadiene, 2-ethyl-1,3-butadiene, 2,3-dimethyl-1,3-butadiene, isoprene, 1,3-pentadiene, chloroprene, 1,3-octadiene, and so forth.

In the method of the present invention, the form of the palladium compounds to be used as the principal catalyst and their atomic valence condition are not so restrictive, and the followings may be exemplified: metallic palladium such as palladium black, palladium metals with carrier, etc.; zero-valence palladium complexes such as bis(t-butylisonitrile)palladium (O), bis(t-amylisonitrile)palladium (O), bis(cyclohexylisonitrile)palladium (O), bis(phenylisonitrile)palladium (O), bis(p-tolylisonitrile)palladium (O), bis(2,6-dimethylphenylisonitrile)palladium (O), tetrakis(triphenylphosphine)palladium (O), tetrakis(triphenylphosphite)palladium (O), tris(dibenzylidene acetone)dipalladium (O), (1,5-cyclooctadiene)(maleic anhydride)palladium (O), bis(norbornene)(maleic anhydride)palladium (O), bis(- maleic anhydride)(norbornene)palladium (O), (dibenzylidene acetone)(bipyridyl)palladium (O), (p-benzoquinone)(o-phenanthroline)palladium (O), and so forth; inorganic salts of palladium such as palladium chloride (II), palladium nitrate (II), tetra-ammine dichloropalladium (II), disodium tetrachloropalladium (II), and others; palladium carboxylates such as palladium acetate (II), palladium benzoate (II), palladium α-picolinate (II), and so on; chelate compounds of palladium such as bis(acetylacetone)palladium (II), bis(8-oxyquinoline)palladium (II), and so on; divalent palladium complexes such as bis(aryl)palladium (II), (η-aryl) (η-cyclopentadienyl)palladium (II), (η-cyclopentadienyl)(1,5-cyclooctadiene)palladium (II) tetrafluoroborate, bis(benzonitrile)palladium (II) acetate, di-μ-chloro-dichloro-bis(triphenyl phosphine)dipalladium (II), bis(tri-n-butylphosphine)palladium (II) acetate, 2,2'-bipyridyl palladium (II) acetate, and so forth; and others.

The quantity of these palladium compounds to be used may be varied in a wide range. Usually, however, it is chosen appropriately in a range of from 0.00001 to 1 gram atom converted in terms of the atomic palladium per 1 mole of conjugated alkadiene, or perferably from 0.0001 to 0.5 gram atom.

For phosphine or phosphite to be used as the cocatalyst for the purpose of the present invention, there may be exemplified the following: tri-alkylphosphine such as tri-n-octylphosphine, tributylphosphine, dimethyl-n-octylphosphine, and others; tricycloalkylphosphine such as tricyclohexylphosphine, and so on; triaryl phosphine such as triphenyl phosphine, tritolyl phosphine, diphenyl-p-chlorophenyl phosphine, tris(p-methoxyphenyl)phosphine, and so forth; tertiary alkylaryl phosphine such as diphenylethyl phosphine, dimethylphenyl phosphine, bis(diphenyl phosphino)methane, 1,2-bis(-diphenyl phosphino)ethane, and so on; phosphites corresponding to the above-mentioned phosphines; alkoxyaryl phosphine such as diethoxyphenyl phosphine, ethoxydiphenyl phosphine, dimethoxyphenyl phosphine, diisopropoxyphenyl phosphine, bis(2-butoxy)-phenyl phosphine, and so forth; aryloxyalkyl phosphine such as diphenoxyethyl phosphine, and others; phosphine containing therein hetero-atoms such as diethylaminopropyldiphenyl phosphine, morpholinopropyldiphenyl phosphine, ethylsulfonyl ethyldiphenyl phosphine, and so forth; and cyclic phosphite to be represented by the following general formula [I] or [II]:

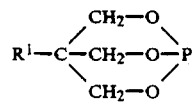

[I]

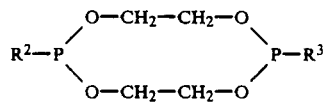

[II]

(where: $R^1$, $R^2$ and $R^3$ denote respectively the alkyl group such as methyl, ethyl, nonyl, etc.; the aryl group such as phenyl, tolyl, naphthyl, etc.; the hydroxyalkyl group such as hydroxymethyl, hydroxyethyl, hydoxypentyl, etc.; the alkoxyalkyl group such as ethoxymethyl, etc.; the aryloxyalkyl group such as phenoxymethyl, etc.; or the acyloxyalkyl group such as acetoxypentyl, etc.).

These phosphines and phosphites are usually used at a ratio of from 0.1 to 100 mols or so with respect to 1 gram atom of palladium, or preferably from 0.1 to 10 mols or so, although the range is not so restrictive.

Carbon dioxide to be used in the method of the present invention may be such one that is present in the reaction system in any form as carbon dioxide, and it can be supplied in any mode as appropriate to the occasion. Examples of such carbon dioxide are: molecular carbon dioxide, carbonic acid, carbonate, bicarbonate, or adducts of carbon dioxide or carbonic acid and amine, and so forth. The upper limit of the quantity of carbon dioxide to be used is determined for the economical reasons, hence use of an excessive amount of carbon dioxide is not particularly detrimental to the reaction to proceed. It is usually used at 1 mol or above with respect to 1 gram atom of palladium, or preferably 10 mols or above.

In the practice of the method according to the present invention, solvent is not always required for the reaction, but, for the smooth execution of the reaction, use of such solvent is preferred. Examples of such solvent are: ethers such as diethyl ether, dioxane, tetrahydrofuran, ethylene glycol dimethyl ether, tetraethylene glycol dimethyl ether, and so on; ketones such as acetone, methyl ethyl ketone, diethyl ketone, methylisopropyl ketone, ethyl-n-butyl ketone, and so forth; nitriles such as acetonitrile, propionitrile, benzonitrile, and so forth; aromatic hydrocarbons such as benzene, toluene, xylene, ethylbenzene, and others; alkanes such as pentane, hexane, heptane, and so on; alkenes such as hexene, octene, and so on; sulfoxides such as dimethylsulfoxide, etc.; nitro compounds such as nitrobenzene, nitromethane, etc.; pyridine derivatives such as pyridine, α-picolin, etc.; and amides such as acetamide, propionamide, N,N-dimethylformamide, N,N-dimethylacetamide, N,N-diethylacetamide, and so forth. Besides these, there may be exemplified: alcohols such as methanol, ethanol, n-propanol, isopropanol, n-butanol, iso-butanol, t-butanol, n-octanol, and so on; and carboxylic acids such as formic acid, acetic acid, propionic acid, lactic acid, and so forth. Of these various solvents, particular care should be taken when use is made of lower alcohols, which accompanies by-products such as alkoxyoctadiene, etc., and when use is made of lower carboxylic acid, which accompanies by-products such as acyloxyoctadiene, etc., both making the reaction system complicated.

The reaction temperature for the reaction of the conjugated alkadiene and water according to the present invention may be selected in a range of from room temperature to 180° C. or so. More generally, it can be selected in a range of from 50° to 130° C. Further, the reaction pressure may be selected in a range of from the normal pressure to 200 kg/cm² or so. Besides, carbon dioxide, there may be added, for the purpose of the reaction, nitrogen, helium, argon, or other gases which are inert to the reaction.

In accordance with the method of the present invention, alkadienols are produced by hydration and dimerization of conjugated alkadiene, using the reaction materials and under the reaction conditions as mentioned in the foregoing. Liquid reaction product to be obtained from this reaction contains therein the catalyst, alkadienols as the principal product, low boiling point by-products such as alkatrienes, high boiling point byproducts such as dialkadienylether, organic carboxylic acid, esters, etc. Depending on circumstances, the liquid reaction product also contains therein solvent, or unreacted water, or unreacted conjugated alkadiene, or else. Production quantity of each of these high boiling point and low boiling point by-products depends on the reaction conditions, which is usually about a few percent with the conjugated alkadiene as a reference.

According to the method of the present invention, the palladium complex is again fed into the reaction system after it is deposited from at least one part of the above-mentioned liquid reaction product.

As the method for depositing the palladium complex, there may preferably be adopted one, in which one part or major part of the alkadienols in the liquid reaction product is separated by various expedients such as distillation, etc. to concentrate the liquid reaction product, thereby decreasing the dissolving quantity of the palladium complex into the liquid reaction product. When the solvent is used in the reaction, it is preferred that the solvent be separated from this liquid reaction product by distillation. In ordinary case, the high boiling point by-products tend to remain in the liquid reaction product as concentrated.

Further the following methods ① to ④ can be adopted as the method for increasing the depositing quantity of the palladium complex.

① To form a complex having a low solubility with respect to the liquid reaction product, as the palladium complex; i.e., the palladium complex, in which phosphine or phosphite is arranged in a coordinated structure. In order to form such complex, it is preferred that phosphine or phosphite be replenished to the liquid reaction product, depending on necessity, so that such phosphine or phosphite may be present in the liquid reaction product at a ratio of at least three times mol or preferably at least four times mol, with respect to 1 gram atom of palladium.

② To heat the reaction system in a temperature range of from 50° to 150° C. and, depending on necessity, under a pressure or a reduced pressure.

③ To bring the liquid reaction product containing therein the high boiling point by-products into contact with a reducing agent.

④ To bring the liquid reaction product containing therein the high boiling point by-products into contact with a basic substance so as to separate by extraction, in advance, a part of the high boiling point by-products such as organic carboxylic acid, etc., thereby decreasing the dissolving quantity of the palladium complex.

In the case of above ③, use of a hydrogen-releasing reducing agent is recommended. Examples of such hydrogen-releasing reducing agent are: molecular hydrogen, lithium aluminum hydride, sodium borohydride, hydrazin, formaldehyde, formic acid, formic acid ester, isopropyl alcohol, and so forth. The quantity of the reducing agent to be used is not so restrictive, and an appropriate range may usually be from 1 to 1,000 times equivalent or preferably from 10 to 100 times equivalent to palladium. Particularly preferred as the reducing agent is molecular hydrogen which may take a form of a mixture with nitrogen, helium, argon, carbon monoxide, and so on. In the case of using the mixture gas, the reaction can be effected by the flowing system, the blowing system, the pressurized tight closure system, and other appropriate systems. In these systems, the hydrogen partial pressure is selected from an arbitrary range of about 200 kg/cm² or below. While the reaction temperature for the reducing reaction may be selected from a wide range of from 0° to 180° C. or so, it may more generally be selected from a range of from 50° to 130° C. In this way, the divalent palladium complex having high solubility is turned into zero-valent palladium complex of low solubility, whereby its deposition quantity is increased.

In the case of ④ the basic substance to be used can be selected from hydroxides, oxides, alkoxides, carboxylates, carbonates, bicarbonates, and so forth formed of alkali metals, alkaline earth metals, and ammonium ions. More concretely, there may be exemplified: lithium hydroxide, sodium hydroxide, potassium hydroxide, magnesium oxide, calcium oxide, barium oxide, sodium ethoxide, sodium acetate, sodium carbonate, potassium carbonate, calcium carbonate, sodium bicarbonate, and so on.

The basic substance is used in general in the form of its being dissolved in a solvent such as water, etc., although it may also be used in a solid form. When it is used in the form of a solution, there is no particular limitation to the concentration of the basic substances, and a solution of a concentration in a range of from 0.05 to 5 mol/l or so is advantageously used. The quantity of the basic substance to be used is not so restrictive, but it should be desirably in an equal molar ratio or above to that of the high boiling point substances to be treated.

The temperature for the liquid reaction product to be treated in contact with the basic substance ranges from 0° to 150° C., or more preferably from 20° to 100° C. In ordinary case, the contact-treatment is done in a mixed phase of an organic phase and an aqueous phase, hence it is preferred that efficient stirring operation be used additionally. By this contact with the basic substance, the catalytic component remains in the organic phase as it is. In contrast to this, the major portion of the high boiling point by-product moves into the aqueous phase. Therefore, the high boiling point by-product can be easily removed from the reaction system by the phase-separation. In this case, an auxiliary solvent may also be used for the smooth separation of the organic phase and the aqueous phase. The auxiliary solvent to be used can be arbitrarily selected from those organic solvents which are inert to the reaction and easy to separate from the aqueous phase. Concrete examples of such auxiliary solvent are: ethers such as diethyl ether, etc,; aromatic hydrocarbons such as benzene, toluene, etc.; saturated aliphatic hydrocarbons such as pentane, hexane, heptane, octane, and so on; cycloaliphatic saturated hydrocarbons such as cyclohexane, etc.; unsaturated hydrocarbons such as octene, octadiene, octatriene, and so forth; halogenated aliphatic hydrocarbons such as methylene chloride, chloroform, carbon tetrachloride, and so on; and others.

The high boiling point by-product which has moved into the aqueous phase can be easily recovered by first making the aqueous phase acidic with use of, for example, hydrochloric acid, followed by extraction of the same with use of an appropriate solvent.

By this extraction operation using the basic substance to separate beforehand a part of the high boiling point by-products which give mal-effect on the deposition of the palladium complex, it is possible to readily deposit such palladium complex.

Incidentally, it should be noted that the method of increasing the deposit quantity of the palladium complex in the practice of the present invention is not limited at all to the above-mentioned methods ① to ④.

Rather, if it is considered to contribute to more efficient deposition of the palladium complex, two or more of the above-mentioned methods ① to ④ may be combined.

As already mentioned in the foregoing, the method of the present invention is to deposit the palladium complex from at least a part of the liquid reaction product to be obtained by the reaction between conjugated alkadiene and water, after which the complex is fed again into the reaction system. In ordinary case, however, it is preferred that the deposited substance be fed by circulation into the reaction system, after it is once separated from the liquid reaction product.

In this case, the palladium complex as deposited from the liquid reaction product can be readily separated and recovered by the well known technique such as filtration, decantation, or others. One part or the whole part of the palladium complex which has thus been separated and recovered is again fed for the reaction between conjugated alkadiene and water by being dissolved in the above-mentioned solvent reaction, depending on necessity.

According to the method of the present invention, it is possible to prevent circulation and accumulation of the harmful high boiling point substance and to circulate the expensive catalyst for its re-use in the reaction. The palladium complex which has been deposited from the liquid reaction product, when it is supplied again into the reaction system, functions as the highly active catalyst which exhibits effectively its inherent catalytic activity.

In contrast to the fact that the method as disclosed in the Japanese Examined Patent Publication No. 6807/1986 is to separate by extraction the high boiling point byproducts contained in the liquid reaction product, and to circulate the liquid extract residue containing the palladium catalyst into the reaction system without depositing the palladium complex, the method of the present invention, though it is also to circulate the liquid extract residue into the reaction system after palladium complex is deposited, prefers that the liquid extract residue be usually circulated after such deposited substance is separated from the liquid reaction product. According to the method of this invention, it becomes possible to circulate the catalyst into the reaction system with a higher state of its catalytic activity.

With a view to enabling those persons skilled in the art, the following preferred examples are presented. It should, however, be noted that these examples are merely illustrative of the invention and not so restrictive, and that any changes and modifications in the ingredients used and the reaction conditions employed may be made without departing from the ambit of the present invention as set forth in the appended claims.

EXAMPLE 1

A mixture composed of 0.5 mol of 1,3-butadiene, 1 mol of water, 0.6 mol of carbon dioxide, 0.5 milli-mol of bis(acetylacetone) palladium, 2.0 milli-mol of triphenyl phosphine, and 63 ml of dimethylformamide was placed in an electromagnetic induction rotary type autoclave made of stainless steel having an internal volume of 0.3l, and subjected to reaction for three hours at a temperature of 90° C. Analysis of the resulted liquid reaction product through gas chromatography revealed that 0.153 mol of 2,7-octadien-1-ol, and 0.019 mol of 1,7-octadien-3-ol were produced.

Then, 1.0 milli-mol of triphenyl phosphine was added to the thus obtained liquid reaction product, and the batch was subjected to distillation at a bath temperature of 90° C. and under a pressure of 1.8 mmHg to thereby fractionate octadienyl alcohol. Thereafter, the heating operation was conducted for 15 min. at a bath temperature of 120° C. and under a pressure of 1.8 mmHg. A yellow solid substance was found deposited in the bottom liquid. When this bottom liquid was filtered, it was separated into 1.67 g of yellow palladium complex containing therein 0.44 milli gram atom of palladium converted in terms of palladium metal and 1.48 g of filtrate of the distilled bottom liquid. The filtrate contained therein the high boiling point by-products with diocta-dienyl ether and nonatrienic acid as the principal components.

The thus deposited and separated palladium complex was placed again in the autoclave, to which 0.5 mol of 1,3-butadiene, 1 mol of water, 0.6 mol of carbon dioxide, and 63 ml of dimethyl formamide were fed afresh. Then, the reaction was conducted under the same conditions as mentioned above, with the consequence that 0.158 mol of 2,7-octadien-1-ol, and 0.016 mol of 1,7-octadien 3-ol were produced.

EXAMPLE 2

The same procedures as in Example 1 above were followed with the exception that 2.0 milli-mol of triphenyl phosphine was added to the thus obtained liquid reaction product. There was deposited and separated 2.35 g of yellow palladium complex containing therein 0.49 milli gram atom of palladium converted in terms of palladium metal.

EXAMPLE 3

The same procedures as in Example 1 above were followed with the exception that no triphenyl phosphine was added to the thus obtained liquid reaction product. There was then deposited and separated 0.74 g of yellow palladium complex containing therein 0.37 milli-gram atom of palladium converted in terms of palladium metal.

EXAMPLE 4

1.0 milli-mol of triphenyl phosphine was added to the liquid reaction product obtained from the same reaction as in Example 1 above. Then, the batch was treated at a bath temperature of 60° C. and under a pressure of 1.8 mmHg to thereby fractionate low boiling point by products, water, and dimethyl formamide. Then, 10 g of 1.0N aqueous solution of sodium hydroxide was added to 26 g of the resulted distilled bottom liquid. After separation of the liquid, the oil phase was further rinsed with 20 ml of pure water, and then octadienyl alcohol was recovered by distillation from the oil phase containing therein the catalytic component, at a bath temperature of 90° C .and under a pressure of 1.8 mmHg.

It was found that yellow palladium complex was deposited in the distilled bottom liquid, which was separated by filtration. The palladium complex which has been separated by filtration was again put into the autoclave, to which 0.5 mol of 1,3-butadiene, 1 mol of water, 0.6 mol of carbon dioxide, and 63 ml of dimethyl formamide were supplied afresh, and the reaction was carried out under the same conditions as in Example 1 above. This reaction oparation was repeated for four times, the results of which are shown in the following Table 1.

TABLE 1

| Frequency of Reaction | First Time | Second Time | Third Time | Fourth Time |
|---|---|---|---|---|
| Yield (%)[1] of Octadienyl Alcohol | 69 | 65 | 67 | 67 |
| Recovery Rate (%)[2] of Palladium Complex | 98.1 | 98.5 | 97.8 | not done |

NOTE:
[1] with butadiene as a reference

[2] Rate of Recovery (%) = $\dfrac{\text{Quantity of palladium in the palladium complex as deposited and separated (gram atom)}}{\text{Quantity of palladium in the liquid reaction product (gram atom)}} \times 100$

EXAMPLE 5

0.5 milli-mol of triphenyl phosphine was added to the liquid reaction product obtained from the same reaction as in Example 1 above, and octadienyl alcohol was fractionated by distillation of the reaction product at a bath temperature of 90° C. and under a pressure of 1.8 mmHg. 4.60 g of the bottom residue obtained by this fractionating operation, in which the palladium complex remained undeposited, was subjected to the reduction reaction for three hours at a bath temperature of 90° C. and by flowing of hydrogen under a normal pressure. As the result, 2.26 g of yellow palladium complex containing therein 0.45 milli-gram atom of palladium converted in terms of palladium metal was deposited and separated. The thus separeted palladium complex was again put into the autoclave in the same manner as in Example 4 above, and the reaction was conducted repeatedly. The result obtained was as same as that in the preceding Example 4.

It is apparent from the foregoing results of the examples that the palladium complex deposited from the liquid reaction product could be re-used effectively without impairing its catalytic activity.

As has been described in detail in the foregoing, according to the method of the present invention, it is possible to prevent the high boiling point by-products from accumulating in the liquid reaction product, and to thereby repeatedly utilize the palladium complex for the production of the alkadienols, without accompanying deterioration in its catalytic activity. This is realized by depositing the palladium complex from the liquid reaction product to be obtained by the above-mentioned reaction and then feeding the liquid reaction product to the reaction system.

As the consequence of this, the method of the present invention makes it possible to efficiently recover the catalyst for repeated use, hence it is highly advantageous from the economical as well as industrial standpoints.

What is claimed is:

1. In a method for producing alkadienols by the reaction of a conjugated alkadiene and water in the presence of carbon dioxide and a catalyst composed of a palladium compound and a phosphine or a phosphite soluble in an organic solvent, the improvement comprising depositing a palladium complex from at least a part of liquid reaction product obtained by said reaction, and feeding said deposited palladium complex into said reaction system.

2. The method for producing alkadienols according to claim 1, wherein said conjugated alkadiene is selected from the group consisting of 1,3-butadiene, 2-ethyl-1,3-butadiene, 2,3-dimethyl-1,3-butadiene, isoprene, 1,3-pentadiene, chloroprene, and 1,3-octadiene.

3. The method for producing alkadienols according to claim 1, wherein said palladium compound is added to the reaction system in a form selected from the group consisting of metallic palladium, zero-valent palladium complex, inorganic salts of palladium, carboxylates of palladium, chelate compounds of palladium, and divalent palladium complex.

4. The method for producing alkaldienols according to claim 1, wherein the quantity of said palladium compound is in the range of from 0.00001 to 1 gram atom converted in terms of the palladium atom per 1 mol of conjugated alkadiene.

5. The method for producing alkadienols according to claim 1, wherein said phosphine or phosphite is one selected from the group consisting of trialkyl phosphine, tricycloalkyl phosphine, triaryl phosphine, tertiary alkyl-aryl phosphine, phosphites corresponding to said phosphines, alkoxy aryl phosphine, aryloxyalkyl phosphine, phosphine containing therein hetero-atoms, and cyclic phosphite represented by the following general formula or:

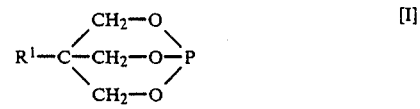

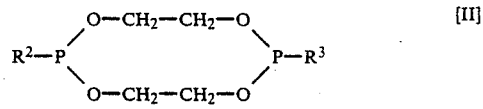

(wherein $R^1$, $R^2$, and $R^3$ denote respectively an alkyl group; and aryl group a hydroxyalkyl group; an alkoxyalkyl group; an aryloxyalkyl group; or an acyloxyalkyl group).

6. The method for producing alkadienols according to claim 1, wherein the quantity of said phosphine or phosphite is in the range of from 0.1 to 100 mols with respect to 1 gram atom of palladium.

7. The method for producing alkadienols according to claim 1, wherein carbon dioxide is fed to the reaction system in the form of molecular carbon dioxide, carbonic acid, carbonate, bicarbonate, or an addition product of carbon dioxide or carbonic acid with amine.

8. The method for producing alkadienols according to claim 1, wherein a reaction solvent is present in the reaction system.

9. The method for producing alkadienols according to claim 8, wherein said reaction solvent is one selected from the group consisting of ethers, ketones, nitriles, aromatic hydrocarbons, alkanes, alkenes, sulfoxides, nitro compounds, pyridine derivatives, amides, alcohols, and carboxylic acids.

10. The method for producing alkadienols according to claim 1, wherein the reaction between the conjugated alkadiene and water is carried out at a temperature ranging from room temperature to 180° C.

11. The method for producing alkadienols according to claim 1, wherein the reaction between the conjugated alkadiene and water is carried out under a pressure in the range of from atmospheric pressure to 200 kg/cm².

12. The method for producing alkadienols according to claim 1, wherein at least one part of the liquid reaction product is heated at a temperature ranging from 50° to 150° C. thereby to deposit the palladium complex.

13. The method for producing alkadienols according to claim 1, wherein three times mols or more of a phosphine or a phosphite with respect to 1 gram atom of palladium is present in at least one part of the liquid reaction product to thereby deposit the palladium complex.

14. The method for producing alkadinenols according to claim 1, wherein at least one part of the liquid reaction product is brought into contact with a reducing agent to thereby deposit the palladium complex.

15. The method for producing alkadienols according to claim 14, wherein said reducing agent is one selected from the group consisting of molecular hydrogen, lithiumaluminum hydride, sodium borohydride, hydrazine, formaldehyde, formic acid, formic acid ester, and or isopropyl alcohol.

16. The method for producing alkadienols according to claim 14 or 15, wherein the contact-treatment with the reducing agent is carried out at a temperature ranging from 0° to 180° C.

17. The method for producing alkadienols according to claim 1, wherein at least one part of the liquid reaction product is brought into contact with a basic substance, thus depositing the palladium complex.

18. The method for producing alkadienols according to claim 17, wherein said basic substance is one selected from the group consisting of hydroxides, oxides, alkoxides, carboxylates, carbonates and bicarbonates formed of alkali metals, alkaline earth metals, and ammonium ions.

19. The method for producing alkadienols according to claim 17 or 18, wherein the contact-treatment with said basic substance is carried out at a temperature ranging from 0° to 150° C.

20. The method for producing alkadienols according to claim 1, wherein said palladium complex is deposited by subjecting at least one part of the liquid reaction product to the following treatment (i) and (ii) of:
   (i) (a) having present a phosphine or a phosphite in said liquid reaction product at a ratio of three times mols or more with respect to 1 gram atom of palladium; and/or
       (b) bringing said liquid reaction product into contact with a reducing agent; and
   (ii) heat-treating said liquid reaction product at a temperature ranging from 50° to 150° C.

21. The method for producing alkadienols according to claim 1, wherein said palladium complex is deposited by subjecting at least one part of the liquid reaction product to the following treatments (i), (ii), and (iii) of:
   (i) (a) having present a phosphine or a phosphite in said liquid reaction product at a ratio of three times mols or more with respect to 1 gram atom of palladium; and/or
       (b) bringing said liquid reaction product into contact with a reducing agent;
   (ii) heat-treating said liquid reaction product at a temperature ranging from 50° to 150° C.; and
   (iii) bringing said liquid reaction product into contact with a basic substance.

22. The method for producing alkadienols according to claim 1, wherein the palladium complex is deposited after concentrating said liquid reaction product by distillation.

23. The method for producing alkadienols according to claim 1, wherein said palladium complex as deposited is fed into the reaction system by recirculation, after having been recovered by separation.

* * * * *